United States Patent
Schulz

(10) Patent No.: US 6,816,252 B2
(45) Date of Patent: Nov. 9, 2004

(54) APPARATUS FOR DETERMINING AN OVERLAY ERROR AND CRITICAL DIMENSIONS IN A SEMICONDUCTOR STRUCTURE BY MEANS OF SCATTEROMETRY

(75) Inventor: Bernd Schulz, Radebeul (DE)

(73) Assignee: Advanced Micro Devices, Inc., Austin, TX (US)

(*) Notice: Subject to any disclaimer, the term of this patent is extended or adjusted under 35 U.S.C. 154(b) by 128 days.

(21) Appl. No.: 10/134,243

(22) Filed: Apr. 29, 2002

(65) Prior Publication Data

US 2003/0043372 A1 Mar. 6, 2003

(30) Foreign Application Priority Data

Aug. 30, 2001 (DE) .......................... 101 42 317

(51) Int. Cl.⁷ .............................................. G01N 21/00
(52) U.S. Cl. ............................. 356/237.5; 356/237.6; 356/237.1
(58) Field of Search ................... 356/399, 400, 356/401, 636; 430/30, 22

(56) References Cited

U.S. PATENT DOCUMENTS

| | | | | |
|---|---|---|---|---|
| 4,656,358 A | * | 4/1987 | Divens et al. ............... 356/636 |
| 5,231,471 A | * | 7/1993 | Torigoe ....................... 356/401 |
| 5,276,337 A | * | 1/1994 | Starikov ...................... 356/401 |
| 5,867,276 A | | 2/1999 | McNeil et al. ............... 356/445 |
| 5,877,276 A | | 3/1999 | Talmadge .................... 356/376 |
| 5,880,838 A | | 3/1999 | Marx et al. .................. 356/351 |
| 6,051,348 A | | 4/2000 | Marinaro et al. ............. 430/30 |
| 6,081,334 A | | 6/2000 | Grimbergen et al. ........ 356/357 |
| 6,151,120 A | * | 11/2000 | Matsumoto et al. ......... 356/400 |
| 6,166,801 A | * | 12/2000 | Dishon et al. ............... 356/400 |
| 6,245,584 B1 | | 6/2001 | Marinaro et al. ............. 438/14 |
| 6,433,878 B1 | | 8/2002 | Niu et al. .................... 356/603 |
| 6,479,371 B2 | * | 11/2002 | Noda ........................... 438/455 |
| 2002/0135781 A1 | | 9/2002 | Singh et al. ................. 356/601 |

* cited by examiner

*Primary Examiner*—Michael P. Stafira
*Assistant Examiner*—Juan D Valentin, II
(74) *Attorney, Agent, or Firm*—Williams, Morgan & Amerson, P.C.

(57) ABSTRACT

An apparatus for obtaining information on critical dimensions and overlay accuracy of features in a semiconductor structure comprises a light source, a detector and an optical means defining a first optical path and a second optical path. The first optical path and the second optical path are oriented in correspondence with the respective orientations of diffracting patterns provided on the semiconductor structure to obtain the required information without the necessity of rotating the semiconductor structure. This insures a significantly higher throughput.

14 Claims, 2 Drawing Sheets

APPARATUS FOR DETERMINING AN OVERLAY ERROR AND CRITICAL DIMENSIONS IN A SEMICONDUCTOR STRUCTURE BY MEANS OF SCATTEROMETRY

BACKGROUND OF THE INVENTION

1. Field of the Invention

The present invention relates to the field of fabrication of integrated circuits, and more particularly, to an apparatus for metrology by means of scatterometry.

2. Description of the Related Art

Fabrication of integrated circuits requires tiny regions of precisely controlled size to be formed in a material layer of an appropriate substrate, such as a silicon substrate. These tiny regions of precisely controlled size are generated by treating the material layer by means of, for example, ion implantation or etching, wherein a mask layer is formed over the material layer to be treated to define these tiny regions. In general, a mask layer may consist of a layer of photoresist that is patterned by a lithographic process. During the lithographic process, the resist may be spin coated onto the wafer substrate, and is then selectively exposed to ultraviolet radiation. After developing the photoresist, depending on the type of resist, positive resist or negative resist, the exposed portions or the non-exposed portions are removed to form the required pattern in the photoresist layer. Since the dimensions of the patterns in modem integrated circuits are steadily decreasing, the equipment used for patterning device features have to meet very stringent requirements with regard to resolution of the involved fabrication processes. In this respect, resolution is considered as a measure specifying the consistent ability to print minimum-size images under conditions of predefined manufacturing variations. One dominant factor in improving the resolution is represented by the lithographic process, in which patterns contained in a photo mask or reticle are optically transferred to the substrate via an optical imaging system. Therefore, great efforts are made to steadily improve optical properties of the lithographic system, such as numerical aperture, depth of focus, and wavelength of the light source used.

The quality of the lithographic imagery is extremely important in creating very small feature sizes. Of comparable importance is, however, the accuracy with which an image can be positioned on the surface of the substrate. Integrated circuits are fabricated by sequentially patterning material layers, wherein features on successive material layers bear a spatial relationship to one another. Each pattern formed in a subsequent material layer has to be aligned to a corresponding pattern formed in the previous material layer within specified registration tolerances. These registration tolerances are caused by, for example, a variation of a photoresist image on the substrate due to non-uniformities in such parameters as resist thickness, baking temperature, exposure and development. Furthermore, non-uniformities in the etching processes can lead to variations of the etched features. In addition, there exists an uncertainty in overlaying the image of the pattern for the current material layer to the etched pattern of the previous material layer, while photolithographically transferring the image onto the substrate. Several factors contribute to the inability of the imagery system to perfectly overlay two layers, such as imperfections within a set of masks, temperature differences between times of exposure, and a limited registration capability of the alignment tool. As a result, the dominant criteria determining the minimum feature size finally obtained are resolution for creating features in individual wafer levels and the total overlay error to which the above-explained factors, in particular the lithographic processes, contribute.

Accordingly, it is essential to steadily monitor the resolution, i.e. the capability of reliably and reproducibly creating the minimum feature size, also referred to as critical dimension (CD), within a specific material layer, and to steadily determine the overlay accuracy of patterns of two subsequently formed material layers. Recently, scatterometry has become a powerful tool in characterizing a periodic pattern of features with a size in the range of 1 $\mu$m to 0.1 $\mu$m. In the scatterometry analysis, the substrate containing a periodic structure is illuminated with radiation of an appropriate wavelength range and the diffracted light is detected. Many types of apparatus may be used for illumination and detecting of the diffracted light beam. U.S. Pat. No. 5,867,276 describes a so-called two-$\theta$ scatterometer wherein the angle of incidence of a light beam is continuously varied by synchronously rotating the sample and the detector. Furthermore, this document describes a lens scatterometer system utilizing a rotating block to translate a light beam emitted from a light source to different points of the entrance aperture of a lens to illuminate the substrate at different angles of incidence. Moreover, this document describes a scatterometer with a fixed angle of incidence that utilizes a multi-wavelength illumination source to obtain the required information from the diffracted multi-wavelength beam. From this information contained in the measurement spectrum, the optical and dimensional properties of the individual elements that form the periodic structure and thickness of underlying films can be extracted, for example, by statistical techniques. The sample parameters of interest may include the width of lines, if the periodic pattern contains lines and spaces, their sidewall angle, and other structural details. In case of a more complex periodic structure having, for example, a two-dimensional periodicity, the parameters may include dimensional properties such as hole diameter or depth. It should be noted that in the present application the term "scatterometer" also includes devices emitting a substantially linearly polarized light beam such as an ellipsometer, to obtain structural information with respect to changes in the polarization state by detecting and analyzing the beam scattered from the periodic structure.

Typically, the diffracting patterns used for metrology of critical dimensions and overlay accuracy exhibit a periodicity along a predefined direction. Accordingly, two diffracting patterns are provided having a periodicity defined along two orthogonal directions to precisely monitor the quality of critical dimensions with respect to both directions. This arrangement, however, requires rotating the substrate and re-aligning the substrate with respect to the measurement tool, such as a spectroscopic ellipsometer, which is frequently used in semiconductor facilities. Rotating and re-aligning the substrate, however, significantly reduces the throughput.

Therefore, a need exists for an apparatus used for metrology of critical dimensions and overlay accuracy that allows precise measurements with high efficiency.

SUMMARY OF THE INVENTION

In view of the problems pointed out above, according to one aspect of the present invention an apparatus is provided for measuring critical dimensions and overlay errors in a semiconductor structure, wherein the semiconductor structure includes a first diffracting pattern oriented in a first direction and second diffracting pattern oriented in the second direction. The apparatus in accordance with the present invention comprises a light source for emitting at least one light beam, a first plurality of deflecting elements defining a first optical path to direct a first light beam to the first diffracting pattern and a second plurality of deflecting elements defining a second optical path to direct a second light beam to the second diffracting pattern. The apparatus further comprises a detector optically connectable to the first and second optical paths to receive a light beam diffracted by the first and second diffracting patterns, respectively.

According to a second aspect of the present invention, an apparatus is provided for obtaining information on critical dimensions and overlay accuracy of features formed in a semiconductor structure, wherein the semiconductor structure includes a first diffracting pattern oriented with respect to a first direction and a second diffracting pattern oriented with respect to a second direction. The apparatus comprises a light source for emitting at least one light beam and at least one optical fiber to define a first optical path and second optical path. In addition, the apparatus comprises a detector optically connectable to the first and second optical paths to receive a light beam diffracted by the first and the second diffracting patterns, respectively.

The apparatus in accordance with the present invention allows the detection of first and second light beams that are diffracted by the differently-oriented first and second diffracting patterns. Thus, a time consuming rotation of the substrate and a re-alignment is no longer necessary. The present invention is particularly advantageous in combination with existing scatterometers, such as a spectroscopic ellipsometer, since the ellipsometer may be used as both light source and detecting means of the apparatus in accordance with the present invention. Accordingly, to obtain the complete information on critical dimensions or to obtain the full overlay information in case the first and the second diffracting patterns bear information on the overlay accuracy of features formed by means of two subsequent photolithographic processes, one or more measurement sites, i.e., one or more diffracting patterns, can be visited in an uninterrupted sequence. The stage holding the wafer will linearly be moved for the distance between two diffracting patterns without rotation of the wafer. As a result, compared to a conventional apparatus, such as a spectroscopic ellipsometer, a significant increase of throughput is accomplished.

BRIEF DESCRIPTION OF THE DRAWINGS

The invention may be understood by reference to the following description taken in conjunction with the accompanying drawings, in which like reference numerals identify like elements, and in which.

Figure 1:
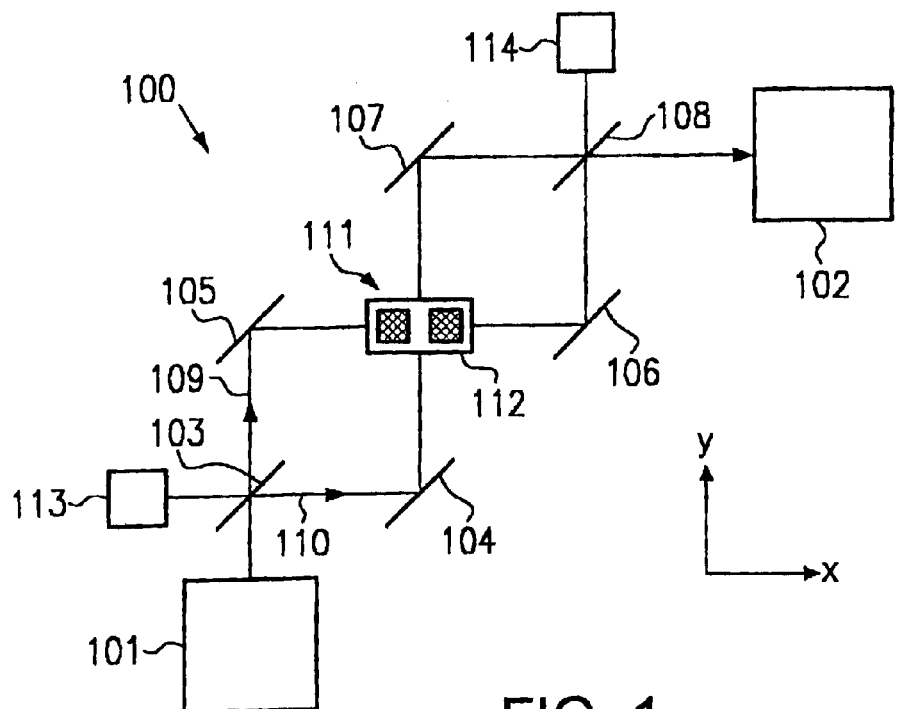
FIG. 1 shows a schematic top view of the optical means of an illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 shows a schematic top view of one embodiment of the present invention. An apparatus 100 for metrology of critical dimensions and overlay accuracy comprises a light source 101 and a detector 102. The light source 101 may be adapted to provide a light beam of a broad spectral composition, or may be adapted to provide a light beam of one or more wavelengths extending over a relatively narrow wavelength range. The detector 102 may comprise one or more dispersive optical elements capable of providing spectrally resolved information regarding a received light beam. In particular, the detector 102 may be adapted to provide information on the polarization state of a received light beam. Moreover, a spectroscopic ellipsometer as used for analyzing optical properties of material layers formed on a semiconductor substrate may be utilized as the light source 101 and the detector 102. A plurality of deflecting mirrors 103–108 define a first optical path 109 and a second optical path 110. At a region 111 where the first optical path 109 and the second optical path 110 intersect, a substrate holder 112 is provided that receives a semiconductor structure including first and second diffracting patterns oriented in two different directions, such as the X-direction and the Y-direction as indicated in FIG. 1, wherein the first optical path 109 corresponds to the X-direction and the second optical path 110 corresponds to the Y-direction. The deflecting mirror 103 and the deflecting mirror 108 are mechanically coupled to a switching means 113 and 114, respectively, to selectively place the deflecting mirror 103 and the deflecting mirror 108 in the first and second optical paths 109 and 110, respectively. A portion of the first optical path 109 that impinges onto the region 111 lies in a first plane of incidence parallel to the X-direction. A portion of the second optical path 110 that impinges onto the region 11 lies in a second plane of incidence parallel to the Y-direction.

In operation, a semiconductor structure, such as a wafer, including differently oriented diffracting patterns is mounted on the substrate holder 112 and is aligned with respect to the X- and Y-directions. The substrate holder 112 is moved to the region 111 and one of the diffracting patterns, for example the pattern corresponding to the X-direction, is adjusted to centrally receive a light beam emitted from the light source 101 and propagating along the first optical path 109. The switching means 113 is actuated to remove the deflecting mirror 103 from the optical path 109. The switching means 113 may comprise a translation stage (not shown) to remove the deflecting mirror 103 by a linear motion, and/or the switching means 113 may comprise a rotational stage (not shown) to remove the deflecting mirror 103 by rotation. Likewise, the switching means 114 is activated to put the deflecting mirror 108 in place to receive a light beam from the deflecting mirror 106 and direct it to the detector 102. After analyzing the light beam diffracted by a first diffracting pattern and directed to the detector 102 by the deflecting mirrors 106 and 108, the switching means 113 is activated to place the deflecting mirror 103 in the optical path 109 to deflect the light emitted from light source 101 to the deflecting mirror 104. The deflecting mirror 104 reflects the light beam to the second diffracting pattern oriented, for example, in the Y-direction. The diffracted light beam is then guided to the detector via the deflecting mirror 107, wherein the switching means 114 is actuated to remove the deflecting mirror 108 from the second optical path 110. Depending on the position of the diffracting patterns, it may be necessary to move the substrate holder 112 in one of the directions X and Y to precisely center the light beam propagating along the first and second optical paths 109 and 110, respectively. In one embodiment, the optical characteristics of the reflecting mirrors 103–108 are substantially identical so that measurement results for the two directions are directly comparable to each other without any influence of the deflecting mirrors 103–108. For this reason, it is advantageous to provide a symmetrical arrangement with respect to the number of deflection mirrors used for defining the first and second optical paths 109 and 110. In the present embodiment, each of the first and second optical paths 109, 110 is defined by three deflections. In particular, for polarization sensitive applications, a symmetrical arrangement is advantageous, since additional reflections in one of the optical paths may lead to a variation of the polarization state of the diffracted beam in a different manner for the first and second optical paths, respectively.

Figure 2:
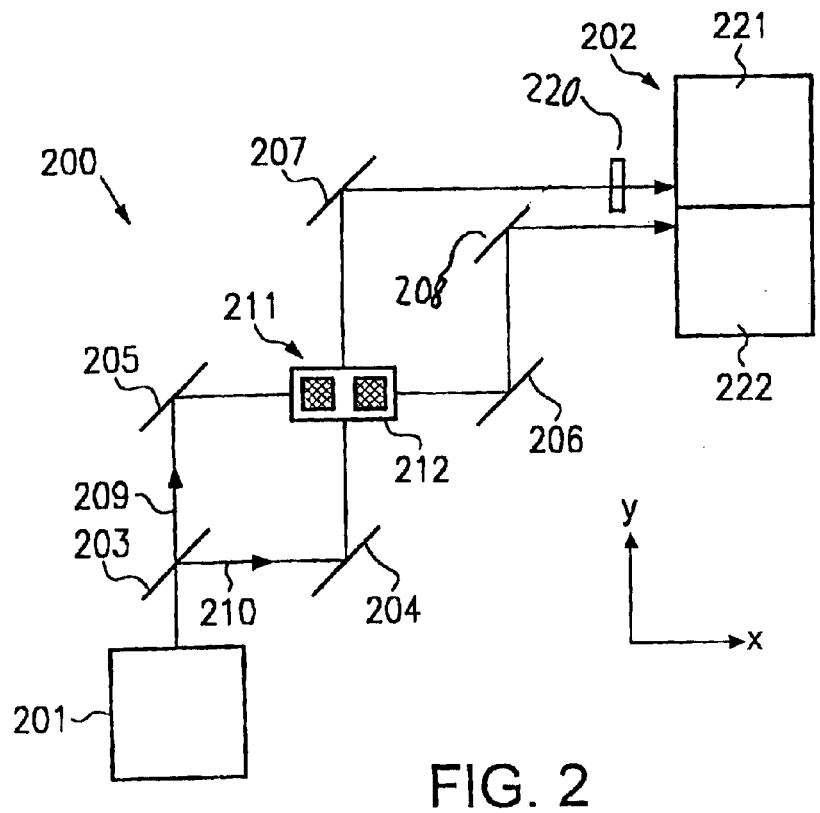
FIG. 2 shows a schematic top view of an illustrative embodiment capable of simultaneously measuring two differently-oriented diffracting patterns.
Figure 3:
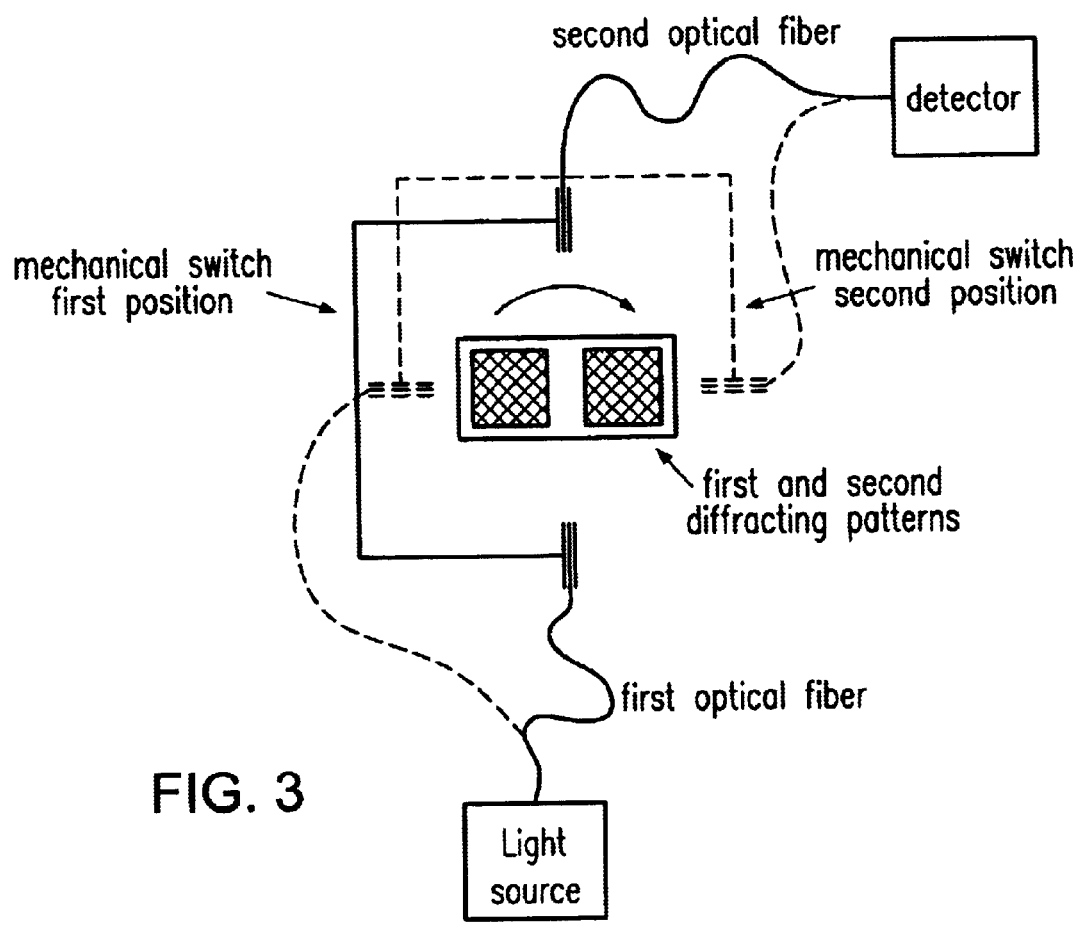
FIG. 3 is a schematic view of another embodiment of the present invention employing a mechanical switch.

FIG. 2 shows a schematic top view of a further illustrative embodiment of the present invention. In FIG. 2, an apparatus 200 for metrology of critical dimensions and overlay accuracy comprises a light source 201, a plurality of deflecting mirrors 203–208 that define, respectively, a first optical path 209 and a second optical path 210. A substrate holder 212 adapted to receive a semiconductor structure such as a wafer is located at a region 211 where the first and second optical paths 209 and 210 intersect. A detector 200 comprises a second detecting portion 221 and a first detecting portion 222 to receive a second and a first deflected light beam. The deflecting mirror 203 is partially transmissive such that a light incident on the deflecting mirror 203 is partially reflected and partially passed through the deflecting mirror 203. The ratio between the transmittance and the reflectivity of the deflecting mirror may, in one embodiment, be selected as substantially 0.5. However, any other ratio for the intensities of light beams propagating along the first and second optical paths 209, 210 maybe used.

An optional transmissive element 220 may be provided in the second optical path 210 to compensate for the additional "transmission event" that a light beam experiences in the first optical path 209 by passing the deflecting mirror 203. By providing the transmissive element 220 the number of reflections and transmissions in the first optical path 209 and in the second optical path 210 is equal. The position of the transmissive element 220 in the second optical path 210 is not critical, and the transmissive element may, for example, be placed between the second detecting portion 221 and the deflecting mirror 207, or between the deflecting mirrors 203 and 204.

In one illustrative embodiment, the combined transmittance of the deflecting mirror 203 and of the transmissive element 220 is selected to substantially match the reflectivity of the deflecting mirror 203, thereby providing a substantially equal light intensity in the first and second optical paths 209, 210.

In operation, a light beam is emitted from the light source 201 and arrives at the deflecting mirror 203 where a portion of the light is deflected to propagate along the second optical path 210 to the deflecting mirror 204. The portion of the incident light beam passing through the deflecting mirror 203 propagates along the first optical path 209 to the deflecting mirror 205. In one illustrative embodiment, the deflecting mirror 203 is designed such that about 50% of the incoming light is reflected and 50% is transmitted. The deflecting mirrors 204 and 205 are positioned such that the light beams reflected therefrom hit the semiconductor structure mounted on the substrate holder 212 at respective diffracting patterns oriented in conformity with the directions of the first and second optical paths 209 and 210. The light diffracted from one diffracting pattern and propagating along the second optical path 210 arrives at the deflecting mirror 207 and is directed to the transmissive element 220, where a portion of the diffracted light, depending on the transmittance of the transmissive element 220, passes through the transmissive element 220 and enters the second detecting portion 221. The light diffracted from the other diffracting pattern and propagating along the first optical path 209 arrives at the deflecting mirror 206 and is reflected to the deflecting mirror 208 where the light beam is reflected to arrive at the first detecting portion 222. It should be noted that the light emitted by the light source 201 and propagating along the first optical path 209 "experiences" the same "deflection and transmission" events as the light beam propagating along the second optical path 201. Accordingly, the measurement results obtained from the second detecting portion 221 and the first detecting portion 222 directly indicate the difference of the differently oriented diffracting patterns. Thus, this embodiment allows to simultaneously obtain information on the critical dimension and/or overlay accuracy of diffracting patterns oriented in two different directions. Moreover, no movable deflecting mirrors are required.

In a further variation, the deflecting mirror 207 is adjusted to direct the light beam to the first detecting portion 222. In the first detecting portion 222 then the spectral characteristics of the combined light beams of the beams diffracted by the differently oriented diffracting patterns are analyzed. Depending on the diffracting characteristics of the diffracting patterns as well as on the spectral characteristics of the light beam provided by the light source 201, a single detecting portion 222 may be sufficient to obtain the required information on the critical dimensions and/or the overlay accuracy. Similarly, the deflecting mirror 206 may be positioned to guide the diffracted light beam to the second detecting portion 221.

In a further variation, the deflecting mirror 207 may mechanically be coupled to an actuator element (not shown) so that the deflecting mirror 207 can be positioned to direct the diffracted light beam selectively to the second detecting portion 221 or the first detecting portion 222. The same applies for the deflecting mirror 206.

It should be noted that other arrangements using 1, 2, 4 or more deflecting mirrors for defining the first and second optical paths may be employed and are within the scope of the present invention. Furthermore, any optical element capable of deflecting a light beam, such as a prism and the like, may be used as the deflecting mirrors.

In a further embodiment not shown in the figures, the apparatus comprises one or more optical fibers to define first and second optical paths. For example, a light source is optically coupled to first optical fiber that represents a portion of a first optical path and guides the light beam to a first diffracting area. A second optical fiber coupled to receive a light beam from the light source is arranged to supply the light beam to a second diffracting area that is oriented in a different direction than the first diffracting area. The light beam provided, for example, by a spectroscopic ellipsometer, may be coupled into the first and second optical fibers sequentially or simultaneously. Preferably, the first and second optical fibers are of the polarization maintaining type. The beams diffracted by the first and second diffracting areas are advantageously coupled into respective optical fibers to guide the beams to a detector means. If a single channel detector is employed, i.e., a detector for analyzing one light beam at a time, the optical fibers at the detector side may be combined by a fiber coupler combining the optical fibers. Thus, an existing spectroscopic ellipsometer may be used for determining diffracting characteristics of differently oriented diffracting areas, either sequentially or simultaneously.

In a further embodiment not shown in the figures, the apparatus comprises a first optical fiber, a second optical fiber and a switch mechanically coupled to one end of the first and second optical fibers. In a first position, the switch defines a first optical path to supply a light beam in a first plane of incidence to a diffracting area and to lead light diffracted by the diffracting area to a detector. In a second position, the switch defines a second optical path to supply a light beam in a second plane of incidence to the diffracting area and to lead light diffracted by the diffracting area to the detector. The switch may comprise a rotary element that may be rotated by an angle of about 90° in the plane defined by the surface of the diffracting area. The flexibility of the first and second optical fibers allows a rapid change between the first and second positions and, therefore, a quick measurement with different optical paths, i.e., different planes of incidence, can be carried out.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An apparatus for obtaining information on critical dimensions and overlay accuracy of features formed in a semiconductor structure, wherein the semiconductor structure includes a first diffracting pattern oriented with respect to a first direction and a second diffracting pattern oriented with respect to a second direction, the apparatus comprising:
   a light source for emitting at least one light beam;
   a first plurality of deflecting elements defining a first optical path in a first plane of incidence corresponding to the first direction, and a second plurality of deflecting elements defining a second optical path in a second plane of incidence corresponding to the second direction;
   a detector optically connectable to the first and second optical paths to receive a light beam diffracted by the first and the second diffracting patterns, respectively; and
   a first partially reflecting mirror directing a first portion of an incident light beam into the first optical path and directing a second portion of the incident light beam into the second optical path, wherein a common transmittance of the first partially reflecting mirror and of a transmissive element arranged in the second optical path is substantially equal to a reflectivity of the first partially reflecting mirror.

2. The apparatus of claim 1, further comprising first and second actuable deflecting mirrors that are selectively placed in the first and second optical paths, respectively.

3. The apparatus of claim 1, wherein the light source is adapted to emit substantially linearly polarized light.

4. The apparatus of claim 1, wherein the light source is a multi-wavelength light source.

5. The apparatus of claim 1, wherein the light source is adapted to emit a first light beam and a second light beam, the first and second light beams propagating along the first and second optical paths, respectively.

6. The apparatus of claim 1, wherein the detector comprises at least a first and a second detecting portion to simultaneously detect a light beam diffracted by the first and second diffracting patterns.

7. The apparatus of claim 1, wherein the first and second portions of the incident light are substantially equal.

8. The apparatus of claim 1, further comprising an actuator element mechanically coupled to one of the deflecting mirrors to select one of the first and second detecting portions for a light beam propagating along one of the first and the second optical paths.

9. The apparatus of claim 1, wherein the first plurality of deflecting elements comprises at least one reflecting mirror, and wherein the second plurality of deflecting elements comprises at least one reflecting mirror.

10. An apparatus for obtaining information on critical dimensions and overlay accuracy of features formed in a semiconductor structure, wherein the semiconductor structure includes a first diffracting pattern oriented with respect to a first direction and a second diffracting pattern oriented with respect to a second direction, the apparatus comprising:
    a light source for emitting at least one light beam;
    a first optical path and second optical path;
    a detector optically connectable to the first and second optical paths to receive a light beam diffracted by the first and the second diffracting patterns, respectively;
    a first optical fiber with a first end thereof optically coupled to the light source to at least partially define said first optical path;
    a second optical fiber with a first end thereof optically coupled to the detector to at least partially define said second optical path; and
    a switch mechanically coupled to a second end of the first and second optical fibers, respectively; wherein a first position of the switch defines the first optical path and a second position defines the second optical path.

11. The apparatus of claim 10, wherein the switch comprises a rotary element rotatable in a plane perpendicular to the first and second plane of incidence.

12. An apparatus adapted for obtaining information on critical dimensions and overlay accuracy of features formed in a semiconductor structure, wherein the semiconductor structure includes a first diffracting pattern oriented with respect to a first direction and a second diffracting pattern oriented with respect to a second direction, the apparatus comprising:
    means for emitting at least one light beam;
    means for defining a first optical path and second optical path;
    means for receiving a light beam diffracted by the first and the second diffracting patterns, said means for receiving said light beam comprises a detector optically connectable to the first and second optical path;
    a first optical fiber with a first end thereof optically coupled to the means for emitting at least one light beam;
    a second optical fiber with a first end thereof optically counted to the detector; and
    a switch mechanically coupled to a second end of the first and second optical fibers, respectively, wherein a first position of the switch defines the first optical path and a second position defines the second optical path.

13. The apparatus of claim 12, wherein said means for defining said first optical path and said second optical path comprises at least one optical fiber.

14. The apparatus of claim 12, wherein the switch comprises a rotary element rotatable in a plane perpendicular to the first and second plane of incidence.

* * * * *

UNITED STATES PATENT AND TRADEMARK OFFICE
CERTIFICATE OF CORRECTION

PATENT NO. : 6,816,252 B2
DATED : November 9, 2004
INVENTOR(S) : Bernd Schulz

It is certified that error appears in the above-identified patent and that said Letters Patent is hereby corrected as shown below:

Column 8,
Line 50, "path" should be -- paths --.
Line 55, "counted" should be -- coupled --.

Signed and Sealed this

First Day of February, 2005

JON W. DUDAS
*Director of the United States Patent and Trademark Office*